(12) United States Patent  (10) Patent No.: US 7,654,669 B2
Suzuki  (45) Date of Patent: Feb. 2, 2010

(54) OPHTHALMIC PHOTOGRAPHY APPARATUS

(75) Inventor: Takayoshi Suzuki, Hamamatsu (JP)

(73) Assignee: Kowa Kabushiki Kaisha (JP)

( * ) Notice: Subject to any disclaimer, the term of this patent is extended or adjusted under 35 U.S.C. 154(b) by 195 days.

(21) Appl. No.: 11/922,708

(22) PCT Filed: Jun. 7, 2006

(86) PCT No.: PCT/JP2006/311387

§ 371 (c)(1),
(2), (4) Date: Dec. 21, 2007

(87) PCT Pub. No.: WO2007/004383

PCT Pub. Date: Jan. 11, 2007

(65) Prior Publication Data

US 2009/0225276 A1 Sep. 10, 2009

(30) Foreign Application Priority Data

Jul. 1, 2005 (JP) ............... 2005-193337

(51) Int. Cl.
*A61B 3/14* (2006.01)
(52) U.S. Cl. .................. 351/206; 351/212; 351/221
(58) Field of Classification Search ............... 351/205, 351/206, 210, 212, 221
See application file for complete search history.

(56) References Cited

U.S. PATENT DOCUMENTS 5,118,179 A * 6/1992 Sano et al. .................. 351/206
2004/0263781 A1 * 12/2004 Suzuki et al. ............... 351/206

* cited by examiner

*Primary Examiner*—Huy K Mai
(74) *Attorney, Agent, or Firm*—Adams & Wilks

(57) ABSTRACT

To observe interference stripes produced by tear fluid, a low magnification light source 10 is turned on to illuminate the outermost layer of a tear film on the cornea Ec of a subject's eye. Light reflected from the cornea Ec forms an image on a CCD 16, and an interference stripes pattern 18a created by the lipid film on the cornea is displayed on a monitor 18. To measure the amount of tear fluid, light-emitting elements 20a, 20b of a high-magnification light source are turned on to irradiate a tear fluid meniscus Em that has accumulated on the lower eyelid portion of the anterior ocular segment. Light reflected on the surface of the meniscus Em forms an image on the CCD 16, and images 18b, 18c of the light-emitting elements 20a, 20b are displayed on the monitor 18 as clear images separated by an interval D. The amount of tear fluid can be quantitatively measured by measuring the interval D. A single such structure allows interference stripes created by the tear film of the anterior ocular segment to be observed and the amount of tear fluid to be measured.

18 Claims, 2 Drawing Sheets

OPHTHALMIC PHOTOGRAPHY APPARATUS

CROSS-REFERENCE TO RELATED APPLICATIONS

This application is a U.S. national stage application of International Application No. PCT/JP2006/311387, filed Jun. 7, 2006, claiming a priority date of Jul. 1, 2005, and published in a non-English language.

TECHNICAL FIELD

The present invention relates to an ophthalmic photography apparatus, and more specifically to an ophthalmic photography apparatus for photographing the anterior ocular segment of a subject's eye for the purpose of diagnosing dry eye and the like.

BACKGROUND ART

When a subject's eye is affected by dry eye, there is a risk that it will complicate corneal epithelial disorders, conjunctival disorders, and various other ophthalmic diseases. Therefore, the anterior ocular segment of a subject's eye is observed or photographed to diagnose the dry eye and other symptoms. For example, the degree of advancement of dry eye is qualitatively diagnosed through observation of interference stripes formed by the tear fluid in the anterior ocular segment of the subject's eye (Patent Document 1). In this case, it is known that the anterior ocular segment can be satisfactorily observed or photographed when a beam of light incident on the cornea via a projection system is made to enter the surface of the cornea in a vertical direction in order to efficiently condense reflection from the cornea (Patent Document 2).

Furthermore, a lattice-shaped slit is projected on the anterior ocular segment of a subject's eye, and the physical quantity of tear fluid accumulated on the anterior ocular segment is quantitatively measured to diagnose dry eye based on the aperture image of the slit (Patent Document 3).

Patent Document 1: JP-A 1995-136120
Patent Document 2: JP-A 1997-289970
Patent Document 3: JP-A 1999-267102

DISCLOSURE OF INVENTION

Problems to be Solved

However, positions at which the anterior ocular segment is to be illuminated or positions to be observed or photographed are different between the observation of tear film interference stripes according to Patent Document 1 and the measurement of the amount of tear fluid according to Patent Document 3. Furthermore, specific optical systems and different apparatuses have to be used, respectively. When attempts have been made to observe the tear film interference stripes and to measure the amount of tear fluid by a multi-use machine, the lattice-shaped slit placed in the optical system during tear fluid measurement must be removed during the observation of the tear film interference stripes, resulting in a complex configuration and causing the equipment cost to go up.

The present invention has been created in order to solve such problems, and an object thereof is to provide an ophthalmic photography apparatus that has an inexpensive configuration and is capable of observing interference stripes due to a tear film in the anterior ocular segment and measuring the amount of tear fluid.

Means for Solving the Problems

The present invention is characterized by photographing means capable of photographing an anterior ocular segment of a subject's eye at first and second differing magnifications;

a first light source for illuminating the anterior ocular segment of the subject's eye;

a second light source of a plurality of light-emitting elements disposed apart by a prescribed distance for illuminating the anterior ocular segment; and control means for selecting and turning on the first and second light sources;

wherein the anterior ocular segment of the subject's eye is photographed at the first magnification when the first light source is turned on, and photographed at the second magnification when the second light source is turned on.

The present invention is also characterized by a first light source for illuminating the anterior ocular segment of a subject's eye;

a second light source of a plurality of light-emitting elements disposed apart by a prescribed distance for illuminating the anterior ocular segment;

control means for selecting and turning on the first and second light sources; and photographing means for receiving reflected light from a tear film accumulated on the anterior ocular segment to photograph an image formed by the reflected light;

wherein, when the first light source is turned on, the photographing means photographs interference stripes formed by light of reflection from the tear film by the first light source, and, when the second light source is turned on, it photographs a pattern formed by light of reflection from the tear fluid by the light-emitting elements, the pattern being a plurality of striped patterns set apart by an interval corresponding to the distance by which the light-emitting elements are separated from each other.

Effect of the Invention

In the present invention, a plurality of light sources are provided for illuminating an anterior ocular segment, and the light sources are selectively turned on, making it possible to photograph or observe a striped pattern necessary for measuring the tear fluid or interference stripes formed by the tear film of the anterior ocular segment. The symptoms of dry eye can therefore be diagnosed in a diverse manner.

KEY TO SYMBOLS

10 First light source (low-magnification light source)
11 Polarization plate
13 Objective lens
15 Variable power lens 16 CCD (imaging means)
17 Image processor
18 Monitor
19 Controller
20 Second light source (high-magnification light source)

BEST MODE OF CARRYING OUT THE INVENTION

Embodiments of the present invention will be described hereinafter with reference to the drawings.

EMBODIMENT 1

Figure 1:
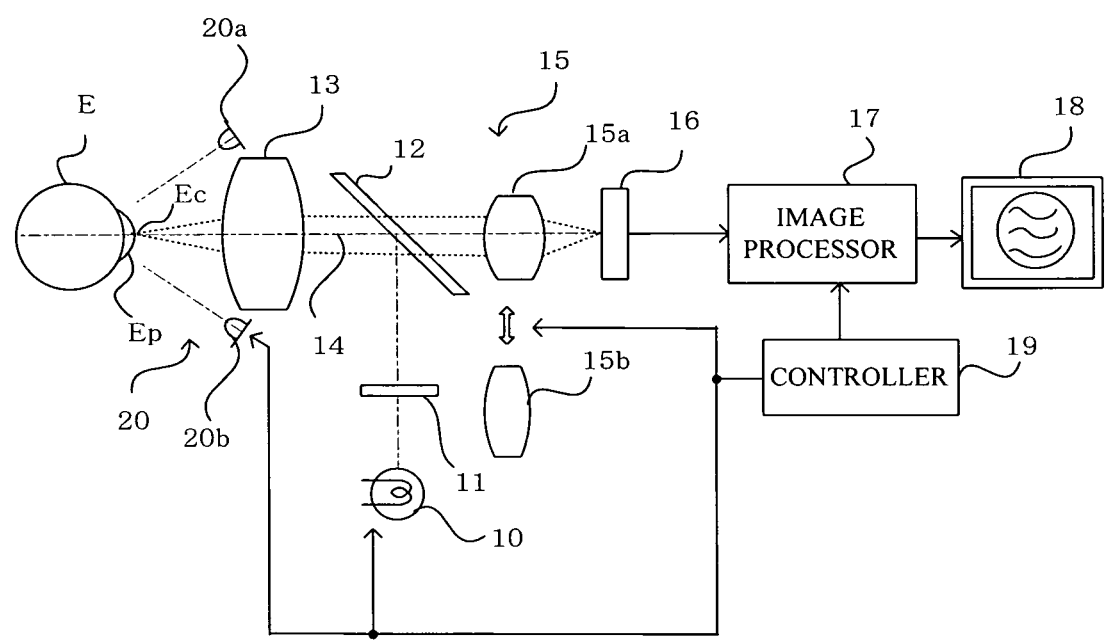
FIG. 1 is a block diagram showing the configuration of an ophthalmic photography apparatus according to the present invention.

FIG. 1 shows a configuration of the ophthalmic photography apparatus according to an embodiment of the present invention. In the drawing, numerical symbol 10 indicates a halogen lamp or other low-magnification light source for use as a first light source. Light from the low-magnification light source 10 passes through a polarization plate 11, is reflected by a half mirror 12 that has a reflection coefficient of about 30% and functions as an optical path splitting means, is made coaxial with an optical axis 14 of a photographing optical system, and is made to irradiate the anterior ocular segment Ep of a subject's eye E via an objective lens 13.

Light reflected from the cornea Ec of the subject's eye E forms an image on a CCD 16 as a photography means, via the objective lens 13, the half mirror 12, and a variable power lens 15. At this time, the optical axis 14 of the photographing optical system is adjusted so as to be at the center of the cornea Ec of the subject's eye.

The variable power lens 15 is composed of a low magnification lens 15a and a high magnification lens 15b, either of which is inserted in the optical path of the photographing optical system. An image signal taken in by the CCD 16 is processed in an image processor 17 and the resulting image is displayed on a monitor 18.

A high-magnification light source 20 used as a second light source is disposed adjacent to the aperture of the objective lens 13. In the present embodiment, the high-magnification light source 20 is composed of two LEDs or other such light-emitting elements 20a and 20b which are separated by a prescribed distance and disposed above and below the aperture of the objective lens 13. The light-emitting elements 20a and 20b are disposed at positions so as to illuminate the lower eyelid portion of the anterior ocular segment when they are turned on.

A controller (control means) 19 controls the insertion and removal of the low magnification lens 15a and the high magnification lens 15b into and from the optical path of the photographing optical system, the switching and turning on of the low-magnification light source 10 and the high-magnification light source 20, and the processing of images. When interference stripes formed by the tear film of the anterior ocular segment are observed, the controller 19 turns on the low-magnification light source 10 (turns off the light-emitting elements 20a and 20b of the high-magnification light source 20), inserts the low magnification lens 15a into the optical path in conjunction with this operation, and instructs the image processor 17 to process images of the interference stripes. When the amount of tear fluid is measured, the controller 19 turns on the high-magnification light source 20 (light-emitting elements 20a and 20b) (turns off the low-magnification light source 10), inserts the high magnification lens 15b into the optical path in conjunction with this operation, and instructs the image processor 17 to measure the amount of tear fluid.

The operation of the apparatus thus configured will next be described separately for a case in which interference stripes are observed and a case in which the amount of tear fluid is measured.

Figure 2A:
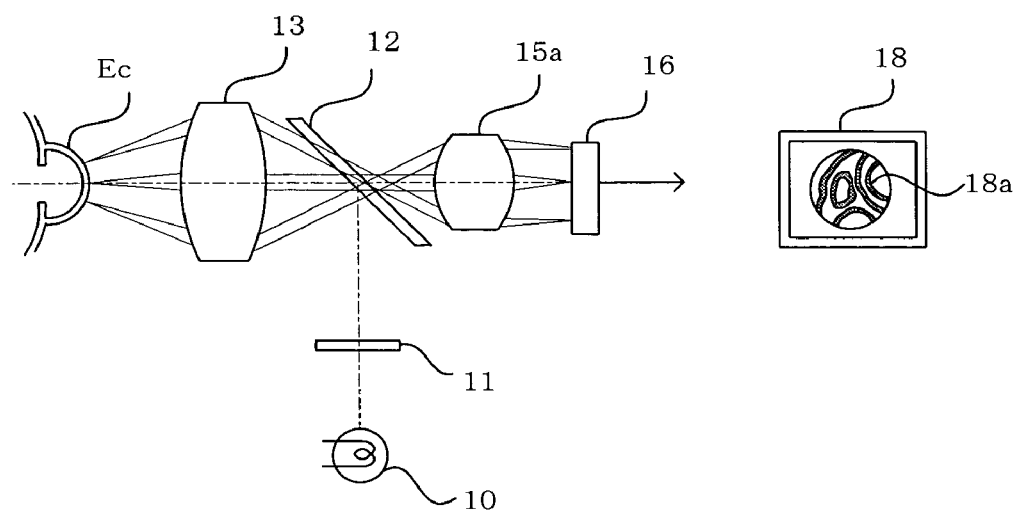
FIG. 2a is a block diagram showing the principle employed when a first light source and a first magnification (low magnification) lens are used to observe interference stripes created by a tear film of the cornea of an anterior ocular segment.

When interference stripes are observed, the low-magnification light source 10 is turned on and the low magnification lens 15a is inserted into the optical path, as shown in FIG. 2a. Light from the light source 10 passes through the polarization plate 11, is reflected by the half mirror 12, and is projected via the objective lens 13 onto the lipid layer of the outermost layer of the tear film on the cornea Ec of the subject's eye. At this time, the illuminating light is made to enter the surface of the cornea in the vertical direction so that the corneal reflection can be efficiently condensed.

Light reflected from the cornea passes through the objective lens 13, the half mirror 12, and the low magnification lens 15a and forms an image on the CCD 16. Light reflected from the cornea forms various interference stripes depending on the thickness of the lipid layer and other conditions, and an interference stripes pattern 18a created by the lipid layer on the cornea is displayed on the monitor 18. In this way the examiner can qualitatively observe the symptoms of dry eye by observing the interference stripes pattern. The details of such a qualitative observation of dry eye are described in Patent Document 1 as mentioned earlier. The state of the cornea can also be quantified by variously processing images of the anterior ocular segment or viewing the video signal amplitude (e.g., refer to JP-A 1997-201334).

Figure 2B:
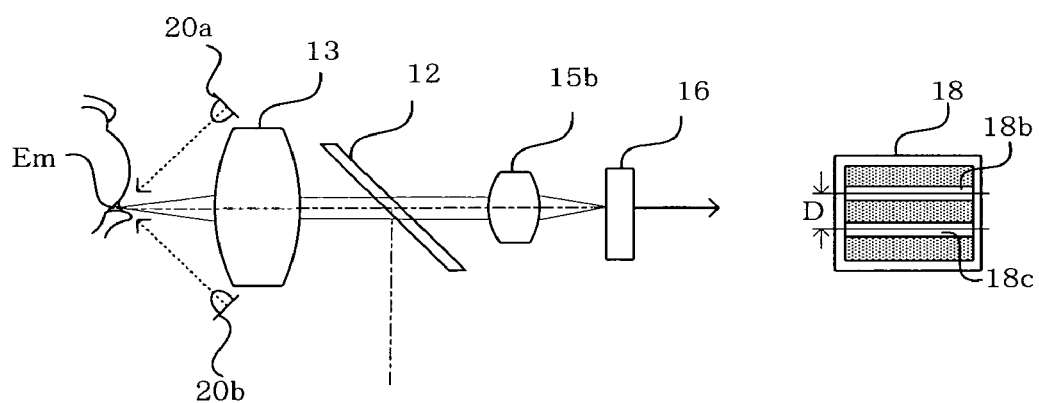
FIG. 2b is a block diagram showing the principle employed when a second light source and a second magnification (high magnification) lens are used to measure the amount of tear fluid on a meniscus of a lower eyelid portion of the anterior ocular segment.

When the amount of tear fluid is measured, the light-emitting elements 20a and 20b of the high-magnification light source are turned on, and the high magnification lens 15b is inserted into the optical path, as shown in FIG. 2b. Light from the light-emitting elements 20a and 20b irradiates a meniscus Em that is formed by the tear fluid accumulated on the lower eyelid portion of the anterior ocular segment. The surface of the tear fluid meniscus Em is changed to a concave shape by the effect of surface tension. The surface therefore performs the role of a concave mirror, and causes the light reflected by the surface of the tear fluid meniscus Em to form an image on the CCD 16 via the objective lens 13, the half mirror 12, and the high magnification lens 15b. This thus causes images 18b and 18c of the light-emitting elements 20a and 20b to be displayed as clear images on the monitor 18. The curvature of the concavity varies according to the amount of tear fluid, causing the interval D between the two clear images 18b and 18c to vary as well. The image formation magnification provided by the high magnification lens 15b can be measured and the amount of tear fluid can be quantitatively measured by measuring the interval D. The details of such a measurement are described in detail in Patent Document 3.

The examiner may, for example, select the use of either light source 10 or light source 20 using a switch or the like. The controller 19 selectively inserts the variable power lens 15a or 15b into the photographing optical path to match the selection of the light source 10 or the light source 20, and switches between the processing methods for the images received by the CCD 16, the displaying methods, and the like in conjunction with the selection.

The invention claimed is:

1. An ophthalmic photography apparatus comprising: photographing means capable of photographing an anterior ocular segment of a subject's eye at first and second differing magnifications;

a first light source for illuminating the anterior ocular segment of the subject's eye;

a second light source of a plurality of lightemitting elements disposed apart by a prescribed distance for illuminating the anterior ocular segment; and control means for selecting and turning on the first and second light sources;

wherein the anterior ocular segment of the subject's eye is photographed at the first magnification when the first light source is turned on, and photographed at the second magnification when the second light source is turned on.

2. An ophthalmic photography apparatus according to claim 1, wherein the plurality of light-emitting elements of the second light source are disposed adjacent to the aperture of the objective lens.

3. An ophthalmic photography apparatus according to claim 1, wherein the first light source is disposed in an optical path that is branched from the optical path of the photography means by an optical path splitting means.

4. An ophthalmic photography apparatus according to claim 1, wherein light from the first light source irradiates the anterior ocular segment of a subject's eye via a polarization plate.

5. An ophthalmic apparatus according to claim 1, wherein the photography means is capable of electronically photographing images, and an image photographed by the photography means is processed differently according to whether the first or the second light source is turned on.

6. An ophthalmic photography apparatus according to claim 5, wherein, when the second light source is turned on, an interval is calculated between stripes of a striped pattern produced by the reflected light of the plurality of light-emitting elements.

7. An ophthalmic photography apparatus comprising:

a first light source for illuminating the anterior ocular segment of a subject's eye;

a second light source of a plurality of lightemitting elements disposed apart by a prescribed distance for illuminating the anterior ocular segment;

control means for selecting and turning on the first and second light sources; and photographing means for receiving reflected light from a tear film accumulated on the anterior ocular segment to photograph an image formed by the reflected light;

wherein, when the first light source is turned on, the photographing means photographs interference stripes formed by light of reflection from the tear film by the first light source, and, when the second light source is turned on, it photographs a pattern formed by light of reflection from the tear fluid by the light-emitting elements, the pattern being a plurality of striped patterns set apart by an interval corresponding to the distance by which the light-emitting elements are separated from each other.

8. An ophthalmic photography apparatus according to claim 7, wherein a cornea of the anterior ocular segment is photographed at low magnification when interference stripes are photographed, and a lower eyelid portion at the anterior ocular segment is photographed at high magnification when a plurality of striped patterns is photographed.

9. An ophthalmic photography apparatus according to claim 8, wherein the plurality of light-emitting elements of the second light source are disposed adjacent to the aperture of the objective lens.

10. An ophthalmic photography apparatus according to claim 9, wherein the first light source is disposed in an optical path that is branched from the optical path of the photography means by an optical path splitting means.

11. An ophthalmic photography apparatus according to claim 10, wherein light from the first light source irradiates the anterior ocular segment of a subject's eye via a polarization plate.

12. An ophthalmic apparatus according to claim 11, wherein the photography means is capable of electronically photographing images, and an image photographed by the photography means is processed differently according to whether the first or the second light source is turned on.

13. An ophthalmic photography apparatus according to claim 12, wherein, when the second light source is turned on, an interval is calculated between stripes of a striped pattern produced by the reflected light of the plurality of light-emitting elements.

14. An ophthalmic photography apparatus according to claim 7, wherein the plurality of light-emitting elements of the second light source are disposed adjacent to the aperture of the objective lens.

15. An ophthalmic photography apparatus according to claim 7, wherein the first light source is disposed in an optical path that is branched from the optical path of the photography means by an optical path splitting means.

16. An ophthalmic photography apparatus according to claim 7, wherein light from the first light source irradiates the anterior ocular segment of a subject's eye via a polarization plate.

17. An ophthalmic apparatus according to claim 7, wherein the photography means is capable of electronically photographing images, and an image photographed by the photography means is processed differently according to whether the first or the second light source is turned on.

18. An ophthalmic photography apparatus according to claim 17, wherein, when the second light source is turned on, an interval is calculated between stripes of a striped pattern produced by the reflected light of the plurality of light-emitting elements.

* * * * *